US008118926B2

(12) United States Patent
Edidin et al.

(10) Patent No.: US 8,118,926 B2
(45) Date of Patent: *Feb. 21, 2012

(54) SELF-FOAMING CEMENT FOR VOID FILLING AND/OR DELIVERY SYSTEMS

(75) Inventors: Avram Allan Edidin, Portola Valley, CA (US); Robert Wenz, Wollstadt (DE); Jorg Meyer, Heusenstamm (DE)

(73) Assignees: Warsaw Orthopedic, Inc., Warsaw, IN (US); Sanatis GmbH, Heusenstamm (DE)

( * ) Notice: Subject to any disclaimer, the term of this patent is extended or adjusted under 35 U.S.C. 154(b) by 221 days.

This patent is subject to a terminal disclaimer.

(21) Appl. No.: 12/366,583

(22) Filed: Feb. 5, 2009

(65) Prior Publication Data
US 2009/0239787 A1    Sep. 24, 2009

Related U.S. Application Data

(63) Continuation of application No. 11/449,047, filed on Jun. 8, 2006, now Pat. No. 7,507,286.

(51) Int. Cl.
C04B 12/02    (2006.01)
C04B 16/08    (2006.01)
C04B 20/00    (2006.01)
C04B 38/00    (2006.01)
C09K 3/00     (2006.01)
A61F 2/28     (2006.01)

(52) U.S. Cl. ........ 106/690; 106/691; 106/672; 106/677; 106/35; 623/23.62

(58) Field of Classification Search ............... 623/23.62; 106/690, 691, 672, 677, 35
See application file for complete search history.

(56) References Cited

U.S. PATENT DOCUMENTS

| | | |
|---|---|---|
| 3,746,680 A | 7/1973 | Boricheski |
| 4,141,864 A | 2/1979 | Rijke et al. |
| 4,192,021 A | 3/1980 | Deibig et al. |
| 4,239,113 A | 12/1980 | Gross et al. |
| 4,341,691 A | 7/1982 | Anuta |
| 4,404,327 A | 9/1983 | Crugola et al. |
| 4,518,430 A | 5/1985 | Brown et al. |
| 4,588,583 A | 5/1986 | Pietsch et al. |
| 4,612,053 A | 9/1986 | Brown et al. |
| 4,629,464 A | 12/1986 | Takata et al. |
| 4,678,436 A | 7/1987 | Kondo et al. |
| 4,722,948 A | 2/1988 | Sanderson |
| 4,791,150 A | 12/1988 | Braden et al. |
| 4,872,936 A | 10/1989 | Engelbrecht |
| 4,902,649 A | 2/1990 | Kimura et al. |
| 4,940,689 A | 7/1990 | Ito |
| 4,957,352 A | 9/1990 | Yasuda et al. |
| 4,959,104 A | 9/1990 | Iino et al. |
| 5,004,501 A | 4/1991 | Faccioli et al. |
| 5,108,956 A | 4/1992 | Inoue et al. |
| 5,149,368 A | 9/1992 | Liu et al. |
| 5,160,371 A | 11/1992 | Ito |
| 5,171,720 A | 12/1992 | Kawakami |
| 5,179,065 A | 1/1993 | Ito |
| 5,204,382 A | 4/1993 | Wallace et al. |
| 5,205,928 A | 4/1993 | Inoue et al. |
| 5,226,877 A | 7/1993 | Epstein |
| 5,262,166 A | 11/1993 | Liu et al. |
| 5,276,070 A | 1/1994 | Arroyo |
| 5,281,265 A | 1/1994 | Liu |
| 5,352,715 A | 10/1994 | Wallace et al. |
| 5,462,356 A | 10/1995 | Murray |
| 5,462,722 A | 10/1995 | Liu et al. |
| 5,522,893 A | 6/1996 | Chow et al. |
| 5,545,254 A | 8/1996 | Chow et al. |
| 5,605,713 A | 2/1997 | Boltong |
| 5,650,108 A | 7/1997 | Nies et al. |
| 5,695,729 A | 12/1997 | Chow et al. |
| 5,795,922 A | 8/1998 | Demian et al. |
| 5,797,873 A | 8/1998 | Franz et al. |
| 5,814,683 A | 9/1998 | Branham |
| 5,847,046 A | 12/1998 | Jiang et al. |
| 5,914,356 A | 6/1999 | Erbe |
| 5,952,010 A | 9/1999 | Constantz |
| 6,002,065 A | 12/1999 | Constantz et al. |
| 6,075,067 A | 6/2000 | Lidgren |
| 6,124,373 A | 9/2000 | Peter et al. |
| 6,153,664 A | 11/2000 | Wise et al. |
| 6,187,046 B1 | 2/2001 | Yamamoto et al. |
| 6,203,574 B1 | 3/2001 | Kawamura |
| 6,206,957 B1 | 3/2001 | Driessens et al. |
| 6,224,635 B1 | 5/2001 | Ricci et al. |
| 6,231,615 B1 | 5/2001 | Preissman |
| 6,241,734 B1 | 6/2001 | Scribner et al. |

(Continued)

FOREIGN PATENT DOCUMENTS

DE    29607832    10/1996

(Continued)

OTHER PUBLICATIONS

Ishikawa et al., "Non-decay type fast-setting calcium phosphate cement: Hydroxyapatite putty containing an increased amount of . . . ," J Biomed Mater Res, 36, 393-399, 1997.
Ishikawa et. al., "Effects of neutral sodium hydrogen phosphate on setting reaction and mechanical strength of hydroxyapatite putty," J Biomed Mater Res, 44, 322-329, 1999.
International Search Report ; WIPO; Jan. 22, 2009.
Abdullah et al., Biodegradable Polymeric Bone Cement Formed from Hydroxyapatite, Poly (Propylene Fumerate), Poly (Vinyl Pyrrolidone) and Benzoyl Peroxide, Materials Science and Technology, vol. 20, No. 9, pp. 1084-1086 (2004) (abstract only).
Baroud et al., Influence of Oscillatory Mixing on the Injectability of Three Acrylic and Two Calcium-Phosphate Bone Cements for Vertebroplasty, J Biomed Mater Res, vol. 68B, No. 1, pp. 105-111 (2004) (abstract only).
Beruto et al., Use of Alpha-Tricalcium Phosphate (TCP) as Powders and as an Aqueous Dispersion to Modify Processing, Microstructure, and Mechanical Properties of Polymethylmethacrylate (PMMA) Bone Cements and to Produce Bone-Substitute Compounds, J Biomed Mater Res, vol. 49, No. 4, pp. 498-505 (2000) (abstract only).

(Continued)

Primary Examiner — Shuangyi Abu Ali

(57) ABSTRACT

A self-foaming bone cement is described herein. In one variation, the bone cements include a self setting calcium phosphate cement formulation which when cured, forms macroscopic pores of varying sizes and densities with sufficient surface area to provide substantial regions for bone turnover.

20 Claims, No Drawings

U.S. PATENT DOCUMENTS

| | | | |
|---|---|---|---|
| 6,248,110 | B1 | 6/2001 | Reiley et al. |
| 6,273,916 | B1 | 8/2001 | Murphy |
| 6,309,420 | B1 | 10/2001 | Preissman |
| 6,325,992 | B1 | 12/2001 | Chow et al. |
| 6,338,810 | B1 | 1/2002 | Carpena et al. |
| 6,436,143 | B1 | 8/2002 | Ross et al. |
| 6,497,901 | B1 | 12/2002 | Royer |
| 6,521,264 | B1 | 2/2003 | Lacout et al. |
| 6,547,866 | B1 | 4/2003 | Edwards et al. |
| 6,562,755 | B1 | 5/2003 | Halbrook, Jr. et al. |
| 6,593,394 | B1 | 7/2003 | Li et al. |
| 6,613,054 | B2 | 9/2003 | Scribner et al. |
| 6,692,563 | B2 | 2/2004 | Zimmermann |
| 6,908,506 | B2 | 6/2005 | Zimmermann |
| 6,953,594 | B2 | 10/2005 | Lee et al. |
| 6,994,726 | B2 | 2/2006 | Lin et al. |
| 7,008,433 | B2 | 3/2006 | Voellmicke et al. |
| 7,115,163 | B2 | 10/2006 | Zimmermann |
| 7,135,027 | B2 | 11/2006 | Delmotte |
| 7,138,442 | B2 | 11/2006 | Smith et al. |
| 7,160,932 | B2 | 1/2007 | Schilke et al. |
| 7,273,523 | B2 | 9/2007 | Wenz |
| 7,507,286 | B2 * | 3/2009 | Edidin et al. .......... 106/690 |
| 2001/0012968 | A1 | 8/2001 | Preissman |
| 2002/0152929 | A1 | 10/2002 | Burgath et al. |
| 2002/0167480 | A1 | 11/2002 | Johnson et al. |
| 2002/0187104 | A1 | 12/2002 | Li et al. |
| 2002/0191487 | A1 | 12/2002 | Sand |
| 2003/0031698 | A1 | 2/2003 | Roeder et al. |
| 2003/0032964 | A1 | 2/2003 | Watkins et al. |
| 2003/0055512 | A1 | 3/2003 | Genin et al. |
| 2003/0139488 | A1 | 7/2003 | Wojciak |
| 2003/0161858 | A1 | 8/2003 | Lidgren |
| 2003/0180344 | A1 | 9/2003 | Wise et al. |
| 2004/0048947 | A1 | 3/2004 | Lidgren et al. |
| 2004/0122359 | A1 | 6/2004 | Wenz et al. |
| 2004/0157952 | A1 | 8/2004 | Soffiati et al. |
| 2004/0226479 | A1 | 11/2004 | Lyles et al. |
| 2004/0265385 | A1 | 12/2004 | West |
| 2005/0105384 | A1 | 5/2005 | Eder et al. |
| 2005/0142211 | A1 | 6/2005 | Wenz |
| 2005/0199156 | A1 | 9/2005 | Khairoun et al. |
| 2005/0246036 | A1 | 11/2005 | Zimmermann |
| 2005/0256220 | A1 | 11/2005 | Lavergne et al. |
| 2006/0079905 | A1 | 4/2006 | Beyar et al. |
| 2007/0021526 | A1 | 1/2007 | He et al. |
| 2007/0032567 | A1 | 2/2007 | Beyar et al. |
| 2007/0048382 | A1 | 3/2007 | Meyer et al. |
| 2007/0128245 | A1 | 6/2007 | Rosenberg et al. |
| 2007/0191964 | A1 | 8/2007 | Preissman |
| 2007/0254011 | A1 | 11/2007 | Schnabelrauch et al. |

FOREIGN PATENT DOCUMENTS

| | | |
|---|---|---|
| DE | 20218668 | 3/2003 |
| DE | 20218668 U1 | 3/2003 |
| EP | 0473048 A2 | 3/1992 |
| EP | 0511868 A2 | 11/1992 |
| EP | 0520690 A2 | 12/1992 |
| EP | 0543765 A1 | 5/1993 |
| EP | 1002513 A1 | 5/2000 |
| EP | 1 255 576 B | 8/2003 |
| EP | 0835668 B1 | 11/2007 |
| JP | 01320251 | 12/1989 |
| JP | 02116684 | 5/1990 |
| WO | WO9202478 A1 | 2/1992 |
| WO | WO9513835 A1 | 5/1995 |
| WO | WO9614265 A1 | 5/1996 |
| WO | WO0149327 A2 | 7/2001 |
| WO | WO0232827 A1 | 4/2002 |
| WO | WO 02/36518 A | 5/2002 |
| WO | WO03086327 A2 | 10/2003 |
| WO | WO03103734 A1 | 12/2003 |
| WO | WO2004050131 A1 | 6/2004 |
| WO | WO2005009481 A2 | 2/2005 |
| WO | WO2007025633 A2 | 3/2007 |
| WO | WO2007067561 A2 | 6/2007 |

OTHER PUBLICATIONS

Bezzi G. et al., A novel sol-gel technique for hydroxyapatite preparation, Materials Chemistry and Physics, 2003, 78: 816-824, entire document.

Bonfield et al., Hydroxyapatite Composite Biomaterials—Evolution and Applications, Materials World, vol. 5, No. 1, pp. 18-20 (1997).

Brown, et al., A new calcium phosphate, water-setting cement, Cements Research Progress 1986 pp. 352-379 (1987).

Canul-Chuil et al., Comparative Study of Bone Cements prepared with either HA or alpha-TCP and Functionalized Methacrylates, J Biomed Mater Res, vol. 64B. No. 1, pp. 27-37 (2003) (abstract only).

Chu et al., Hydroxyapatite/PMMA Composites as Bone Cements, Biomed Mater Eng, vol. 14, No. 1, pp. 87-105 (2004) (abstract only).

Dalby et al., Initial Interaction of Osteoblasts with the Surface of a Hydroxyapatite-Poly (Methylmethacrylate) Cement, Biomaterials, vol. 22, No. 13, pp. 1739-1747 (2001) (abstract only).

Eule et al., Bioactive Bone Cement: The Solution for Osteolysis and Late Implant Loosening, SRS Annual Meeting: Scientific Program Abstracts, pp. 98 (2002).

Frankenburg et al., Evaluation of Hydroxyapatite/Bis-GMA Bone Cement for Fixation of Cemented Hip Stems, The Third Combined Meeting of the Orthopaedic Research Societies of the USA, Canada, Europe and Japan, Hamamatsu City, Japan (1998).

Grigorian et al., Evolution of Tissue Structures in the Mandible after Implantation of Plate from Polymethylmethacrylate and its Compositions with Hydroxyapatite, Stomatolgiia, vol. 82, No. 2, pp. 10-14 (2003) (abstract only).

Harper et al., Tensile Characteristics of Ten Commerical Acrylic Bone Cements, J Biomed Mater Res:Appl Biomater., vol. 53, pp. 605-616 (2000) (abstract only).

Heness et al., Biocomposites—Bone Cement, Hydroxyapatite and Biomimetic Composites for Bone Repair, Innovative Bioceramics, Materials Forum, vol. 27 (2004) (3 page abstract).

Hitchon et al., Comparison of the Biomechanics of Hydroxyapatite and Polymethylmethacrylate Vertebroplasty in a Cadaveric Spinal Compression Fracture Model, J. Neurosurg, vol. 95, Suppl. 2, pp. 215-220, (2001) (abstract only).

Jager et al., Comprehensive Biocompatibility Testing of a New PMMA-hA Bone Cement Versus Conventional PMMA Cement in Vitro, J. Biomater Sci Polym Ed, vol. 14, No. 11, pp. 1283-1298 (2003) (abstract only).

Lee C L et al., Laser Ablation of Dyed Acrylic Bone Cement, Lasers in Surgery and Medicine, Wiley-Liss, New York, US vol. 20, 3, Jan. 1, 1997, pp. 280-289, XP000694435, ISSN:0196-8092.

Lee R.R. et al, Interactions between bone and hydroxyapatite filled 4 META/MMA-TBB adhesive cement in vitro and in physiological environment, 1996, IEEE Xplore, pp. 18-21, entire document.

Li et al., A Novel Injectable Bioactive Bone Cement for Spinal Surgery: A Developmental and Preclinical Study, J Biomed Mater Res, vol. 52, No. 1,,pp. 164-170 (2000) (abstract only).

Liu et al., Influence of the Aspect Ratio of Bioactive Nanofillers on Rheological Behavior of PMMA-Based Orthopedic Materials, J Biomed Mater Res, vol. 71B, No. 1, pp. 116-122 (2004) (abstract only).

Liao et al., A Fundamental Study on Bioreactions of Sr-HA, Hua Xi Kou Qiang Yi Xue Za Zhi, vol. 20, No. 3, pp. 172-174 183 (2002) (abstract only).

Miyazaki et al., Bioactive PMMA Bone Cement Prepared by Modification with Methacryloxypropyltrimethoxysilane and Calcium Chloride, J Biomed Mater Res, vol. 67A, No. 4, pp. 1417-1423 (2003) (abstract only).

Mousa et al., Biological and Mechanical Properties of PMMA-Based Bioactive Bone Cements, Biomaterials, vol. 21, No. 21, pp. 2137-2146 (2000) (abstract only).

Okada et al., Transmission Electron Microscopic Study of Interface Between Bioactive Bone Cement and Bone: Comparison of Apatite and Wollastonite Containing Glass-Ceramic Filler with Hydroxyapatite and Beta-Tricalcium Phosphate Filler, J Biomed Mater Res, vol. 45, No. 4, pp. 277-284 (1999) (abstract only).

Oonishi et al., Hydroxyapatite Granules Interposed at Bone-Cement Interface in Total Hip Replacements: Histological Study of Retrieved Specimens, J Biomed Mater Res, vol. 53, No. 2, pp. 174-180 (2000) (abstract only).

Patel et al., Comparison of Sintering and Mechanical Properties of Hydroxyapatite and Silicon-Substituted Hydroxyapatite, Key Engineering Materials, 240-242, 919-22 (2003) (abstract only).

Patent Abstract XP-002180738 (1 page total), Park et al., "Compositional effects of CaO-SiO2-P2O5 bioactive cement on hardening and hydroxyapatite formation" Yoop Hakhoechi, 31(5):502-512 (1994).

Patent Abstract XP-002180739 (1 page total), Nippon Electric Glass Co., "Bone-repair material for fast, strong bonding—contains glass and/or crystalline glass powder, a.q. phosphate solution and bond formation promoter" (1992).

The term "PRE-", Merriam-Webster Online Dictionary, at the web: http://www.m-w.com, p. 1-2, Sep. 17, 2006.

Serbetci et al., Mechanical and Thermal Properties of Hydroxyapatite-Impregnated Bone Cement, Turk J Med Sci, vol. 30, pp. 543-549 (2000) (abstract only).

Turner et al., Hydroxyapatite Composite Resin Cement Augmentation of Pedicle Screw Fixation, Clinical Orthopaedics & Related Research, vol. 1, No. 406, pp. 253-261 (2003) (abstract only).

Wong et al., In Vivo Cancellous Bone Remodeling on a Strontium-Containing Hydroxyapatite (sr-HA) Bioactive Cement, J Biomed Mater Res A, vol. 68, No. 3, pp. 513-521 (2004) (abstract only).).

Wong et al., Ultrastructural Study of Mineralization of a Strontium-Containing Hydroxyapatite (Sr-HA) Cement in Vivo, J Biomed Mater Res A, vol. 70, No. 3, pp. 428-435 (2004) (abstract only.

Zhao et al., Surface Treatment of Injectable Strontium-Containing Bioactive Bone Cement for Vertebroplasty, J. Biomed Mater Res B Appl Biomater, vol. 69, No. 1, pp. 79-86 (2004) (abstract only).

International Search Report, WIPO, Jan. 22, 2009.

International Search Report and Written Opinion, International Application No. PCT/US2007/012723, mailed Dec. 3, 2008.

International Search Report and Written Opinion, International Application No. PCT/US2007/008789, mailed Nov. 13, 2008.

International Search Report and Written Opinion, International Application No. PCT/EP2006/007750, mailed Jun. 11, 2007.

International Search Report, International Application No. PCT/US03/38580, mailed May 19, 2004.

International Search Report, International Application No. PCT/US2005/014616, mailed Sep. 12, 2005.

Heini, P.F., et al., "Bone substitutes in vertebroplasty," *Eur. Spine J.*, Jun. 14, 2001, vol. 10, pp. S205-S213.

Li, Y., et al. "Preparation of amorphous calcium phosphate in the presence of poly(ethylene glycol)," *Journal of Materials Science Letters*, 2003, vol. 22, pp. 1015-1016.

* cited by examiner

SELF-FOAMING CEMENT FOR VOID FILLING AND/OR DELIVERY SYSTEMS

CROSS-REFERENCE TO RELATED APPLICATIONS

This application is a continuation of U.S. application Ser. No. 11/449,047, Jun. 8, 2006, the entirety of which is incorporated by reference.

BACKGROUND OF THE INVENTION

Bone and other connective tissue generally derive their structure from an extensive matrix structure. Fibrous bundles that are composed of collagen make up the extensive network that provides bone with tension-resistant behavior. Other materials appear in bone matrixes such as proteoglycans, noncollagenous proteins, lipids and acidic proteins. These materials are associated with a mineral phase consisting primarily of hydroxyapatite and the combination of the materials with hydroxyapatite tend to be poorly crystallized. In other words, bone and tooth minerals are impure forms of hydroxyapatite. In general, the crystals of pure synthetic apatites, geological apatites and many impure synthetically produced apatites are larger and more crystalline than the biological crystals of bone, dentin, cementum and cartilage. The crystals of bone, dentin and cementum are very small, irregularly shaped, very thin plates whose rough average dimensions are approximately 10 to 50 angstroms in thickness, 30 to 150 angstroms in width, and 200 to 600 angstroms in length.

When bone undergoes fracture or degradation, bone tissue undergoes remodeling, which is a process that occurs in mammals wherein bone tissue is continuously renewed throughout the life of those mammals. The process of remodeling occurs through the interplay of osteoblasts (bone forming cells) and osteoclasts (a large multinucleate cell found in growing bone that resorbs bony tissue, such as in the formation of canals and cavities).

There are diseases that affect the remodeling of bone such as osteoporosis. Osteoporosis is a systemic disease of the whole organism, which is essentially expressed by an imbalance of bone formation (i.e., the catabolic pathways of the osteoclasts predominates over the metabolic pathway of the osteoblasts). In other words, the anabolic and catabolic bone restructuring processes are reversed, and more bone material is decomposed by an osteoclastic activity, than is grown by the osteoblastic activity.

One means of attempting to control this reversal of bone formation rate is to deliver systemically effective substances. These include, for example, bisphosphonates and hormone preparations, which may aid in accelerating (or at least maintaining) the bone formation rate, but in the process may also lead to adverse side effects at other parts of the patient. Accordingly, to limit the use of these potentially threatening therapies, it is desirable to find bone substitute materials that not only acts as a bone substitute substance or filler, but that also operate upon surrounding bone cells in such a way that it increases and/or induces the metabolic processes (while slowing catabolic processes), so that the excessive osteoclastic activity is attenuated and osteoblastic activity (the in-growth of bones) is increased.

Thus, much research has been performed on developing different bone filling cement formulations to aid in treating bone diseases such as osteoporosis. The use of these bone cement formulations may be used when performing surgery. There are many types of surgery in which bone cement formulations may be used. For example, back surgery, which includes but is not limited to vertebroplasty and/or kyphoplasty, is a type of surgery where bone cement(s) is/are used.

Researchers and physicians have developed cement formulations that contain calcium phosphate. Calcium phosphate is a material that is used in bone cement that is known to enhance the accretion (growth) of bone to a non-biological surface. When bone cements containing calcium phosphate are used as bone void fillers, the calcium phosphates replace living bone through the bone cascade and remodeling process. Although calcium phosphate cement formulations increase accretion, there are instances where it is desirable to further increase accretion to reverse bone catabolism or wherein a bone injury has occurred.

The rate of replacement and resorption in bone is a function of a plurality of factors, including but not limited to the crystallinity of the bone cement formulations as well as its porosity.

The formulations that are presently in use as bone cements may contain either one or the other of the requisite crystallinity or porosity or neither. However, the bone cements that are used for replacement and resorption tend to lack both adequate crystallinity and porosity. That is, the bone cement formulations may have adequate crystallinity but inadequate porosity or may have adequate porosity but inadequate crystallinity. However, to date, bone cements that have both adequate crystallinity and porosity have not yet been developed. Having adequate porosity means having adequate macroscopic pores of varying sizes and densities that allow for efficient bone remodeling. Moreover, having adequate macroscopic pores of varying sizes can increase bone accretion. Without being bound by a particular theory regarding increased porosity, it is believed that increasing surface area of the bone cement formulation may allow osteoblastic cells to better perform their metabolic function. In particular, an increase in variably sized macroscopic pores may result in enhanced accretion. Moreover, without being bound to a particular theory, it is believed that the bony defects that are created by the macroscopic pores also allow blood to better absorb and provide avenues for the entrance of growth factors and BMP (bone morphogenic protein).

Accordingly, bone filling cement with improved crystallinity and/or porosity may be desirable in various medical applications.

BRIEF SUMMARY OF THE INVENTION

The present invention relates to bone filing cement. In one aspect of the invention, the bone cements comprise a self setting calcium phosphate cement formulation which contains macroscopic pores of varying sizes and densities with sufficient surface area to provide substantial regions for bone turnover.

DETAILED DESCRIPTION OF THE INVENTION

Calcium-strontium-hydroxyphosphate cement (strontium-apatite) preparations are described herein. In one embodiment, the cement comprises a powder mixture (i.e., the dry element), which contains components sodium (Na), potassium (K), calcium (Ca), strontium (Sr), phosphates ($PO_4$) and/or carbonates ($CO_3$), together with an alkali salt or an ammonium salt of phosphoric acid or some other anion, and with water and/or an aqueous solution (i.e., the wet element). In one variation, the powder mixture contains, as a Na-component, $NaHCO_3$, as K-components $KHCO_3$ and/or $K_2HPO_4$, as a Ca-component, $Ca_3(PO_4)_2$ (i.e., TCP), and as Sr-components $SrHPO_4$, and/or strontium carbonate ($SrCO_3$) and/or $Sr_3(PO_4)_2$. Moreover, the powder component optionally further contains hydroxyapatite ($Ca_5(PO_4)_3(OH)$). As the aqueous mixing solution for the formation of the strontium-apatite cement, an aqueous solution of an alkali salt or an ammonium salt of the phosphoric acid is suitable.

Calcium phosphates enhance the accretion of bone to a non-biological surface, and are able to fill voids in bone created after surgery or disease. When used as a bone void filler, calcium phosphates are replaced by living bone through the bone cascade and remodeling processes. The rate of replacement or resorption is a function both of the crystallinity of the material and its porosity.

Thus, the present invention relates to bone cement compositions or formulations as well as methods of preparing self-setting calcium phosphate materials which contain macroscopic pores of varying size and density, thereby creating a foamed structure with a highly increased surface area which provides substantially more regions for bone turnover than the non-foamed analogue. In a variation of one embodiment, pore sizes may typically be in the range of 4 to 200 microns in diameter. In another variation, pore sizes may be in the range of 10 to 100 microns in diameter. It should be understood that other pore sizes are contemplated. In an embodiment, there is a distribution of varying pore sizes in the above mentioned ranges.

A typical composition of the dry element of the present invention includes one or more of the following components: tricalcium phosphate (TCP), strontium hydrophosphate ($SrHPO_4$), strontium phosphate ($Sr_3(PO_4)_2$), strontium carbonate ($SrCO_3$), precipitated hydroxyapatite (pHA), sodium phosphate dibasic ($Na_2HPO_4$), $K_2HPO_4$, and/or a cohesion promoter. The sodium phosphate dibasic and potassium phosphate dibasic may act as a setting accelerator when present in the dry element. Alternatively, these dibasic salts may be to keep a solution acidic, for example, when a buffering capacity is overwhelmed.

The cohesion promoters can be added to either of the wet element or the dry element of the cement prior to mixing. Typical cohesion promoters include soluble starch and/or hyaluronic acid.

Additional components that can be added include $(NH_4)_2CO_3$, $(NH_4)HCO_3$, and/or $M_{2-y}H_yCO_3$ (wherein M is a metal in a +1 oxidation state and y is 0, 1, or 2). Metals that can be added include lithium, sodium, potassium, rubidium, cesium, and/or francium.

Typically, the wet element of the present invention will contain a buffer solution that when mixed with the dry element is able to maintain the mixed components at an acidic pH. A buffer solution that has been found to be suitable is a phosphate buffer, such as dipotassium phosphate dibasic and potassium phosphate monobasic (which has a $pKa_2$ of 7.2). Phosphate buffer is a polyprotic acid that has one of its pKa's close to the physiological pH of a neutral solution (i.e., a pH of 7) so it can be readily made so that the buffer solution is acidic. Phosphate buffer is also a suitable buffer because some of the dry components that are being used in the cement contain phosphates in them. If the ratio of molarities of dipotassium phosphate dibasic to potassium phosphate monobasic (i.e., $K_2HPO_4/KH_2PO_4$) is greater than about 5/3, then the buffer will have a pH that is acidic. Maintaining an acidic pH will allow foaming to occur. While it may be desirable to have an acidic pH for the buffer, in certain application, it may also be desirable that the pH be 5 or higher.

In an embodiment, sufficient buffer should be used so that the dry components do not overwhelm the buffering capacity. In an alternative embodiment, the powder can overwhelm the buffering capacity of the solution as long as there are components in the powder element that allows the solution to stay acidic. As an example, by having the acidic calcium phosphate salt, or the appropriate potassium phosphate salt or an organic acid in the powder, one can maintain the acidic nature of the solution even though the buffering capacity of the buffer would ordinarily be overwhelmed. Using this alternative embodiment should aid one in avoiding the use of too much buffer so that one obtains the requisite bone filling formulation consistency that allows for proper filling of bone.

Although phosphate buffer is suitable for the instant invention, it is contemplated, and therefore within the scope of the invention, that other buffers with pKa's that are somewhat acidic or close to a neutral solution are suitable for the present invention. Examples of these buffers include but are not limited to acetate, propionate, malate (pK2), pyridine, piperazine (pK1), cacodylate, succinate (pK2), MES (2-Morpholinoethanesulfonic acid), citrate (pK3), maleate (pK2), histidine, bis-tris, ethanolamine, ADA (N-[carbamoylmethyl]iminodiacetic acid), carbonate (pK1), ACES (N-(2-acetamido)-2-aminoethanesulfonic Acid), PIPES (Piperazine-1,4-bis(2-ethanesulfonic acid)), MOPSO (3-(N-morpholino)-2-hydroxypropanesulfonic acid), imidazole, BIS-TRIS propane, BES (N,N-Bis(2-hydroxyethyl)-2-aminoethanesulfonic acid), MOPS (3-(N-morpholino)-propanesulfonic acid), HEPES (N-Cyclohexyl-2-aminoethanesulfonic acid), TES (N-Tris(hydroxymethyl)methyl-2-aminoethanesulfonic acid), MOBS (4-(N-morpholino)butanesulfonic acid), DIPSO (3-[N,N-bis(2-hydroxyethyl)amino]-2-hydroxy-1-propanesulfonic acid), TAPSO (3-[N-Tris(hydroxymethyl)methylamino]-2-hydroxypropanesulfonic acid), triethanolamine (TEA), pyrophosphate, HEPPSO (4-(2-Hydroxyethyl)piperazine-1-(2-hydroxypropane sulfonic acid)), tricine, hydrazine, glycylglycine (pK2), and Trizma (tris) buffers.

If a phosphate buffer is used as the wet element, an embodiment of the dry element includes components in the following amounts: 30-70 g tricalcium phosphate (TCP), 10-30 g strontium hydrophosphate ($SrHPO_4$), 3-15 g strontium carbonate ($SrCO_3$), 1-5 g precipitated hydroxyapatite (pHA), 0.5-5 g of sodium phosphate dibasic ($Na_2HPO_4$) 10-30 g $K_2HPO_4$, and/or 0.5 to 5% w/w of a cohesion promoter. If the dry mixture is mixed with a 1 to 1 solution of potassium phosphate buffer containing 4M dipotassium phosphate dibasic and 1.5M potassium phosphate monobasic ($K_2HPO_4$ (4M) $KH_2PO_4$ (1.5M)), the pH will be approximately 6.8. Because of the relatively high molarity of both dipotassium phosphate dibasic and potassium phosphate monobasic, the buffer solution will have good buffering capacity and the amount of dry ingredients shown above will allow the buffer to stay acidic.

In an embodiment, when the above dry components are in an acidic solution, carbon dioxide is generated. The underlying reaction to generate carbon dioxide is $CO_2 + H_2O \leftrightarrows H_2CO_3$. When the above system is acidic the reaction is driven to the left, $CO_2$ is generated and the $CO_2$ escapes into the cement. Because the buffer keeps the pH at a relatively constant level (unless or until the buffer capacity is exceeded), $CO_2$ will continue to be generated until the solution becomes more alkaline (causing the reaction to equilibrate or to move to the right). Likewise, if the buffer capacity is exceeded, the presence of organic acids and/or salts that maintain an acidic environment will allow the formation of $CO_2$ bubbles.

The formation of $CO_2$ in the cement will generate bubbles. Some of the bubbles will escape the cement and some of the bubbles will not escape. The formation of $CO_2$ bubbles will cause the cement to foam, leading to a plurality of different size macroscopic pores of varying sizes and densities. These pores will provide substantial regions for bone turnover leading to better accretion.

An example of mixing dry components with a wet element are described in, for example, U.S. Pat. No. 6,497,901 to Royer, which is incorporated herein by reference in its entirety for all purposes. Other mixing of dry components with a wet element are described in U.S. Pat. No. 5,462,356 to Murray, which is also incorporated herein by reference in its entirety for all purposes.

It is contemplated and therefore within the scope of the present invention that the bone cement may contain additional components. These additional components may include one or more antibiotics such as gentamicin, gentamicin sulfate, erythromycin, tobramycin, vancomycin, cefazolin, oxacillin, cefotaxime, colistin, clindamycin, and/or fusidic acid. In one variation, when the cement of the present invention foams, antibiotic that is added to the mixture will have the tendency to spread uniformly throughout the cement. This can lead to a more uniform release of the antibiotics when it is applied to bone. For example, gentamicin sulfate may be a particularly suitable antibiotic for incorporation into the foaming bone cement for certain applications, since it is wide spectrum antibiotic that can be used to attack a large variety of bacteria.

Alternatively, and/or additionally, additional components that can be added to the bone cement of the present invention include one or more radiopacifier compounds such as barium sulfate, 2-[2',3',5'-triiodobenzoyl]ethyl methacrylate (TIBMA), 3,5-diiodine salicylic methacrylate (DISMA), and/or zirconium (IV) oxide. It is contemplated that other compounds that can be seen under fluoroscopic guidance can be used as radiopacifier compounds.

Furthermore, anticancer agents can be added to the bone cement including, but not limited to, 6-mercaptopurine, methotrexate and/or cisplatin.

Other components that can be added include re-enforcing materials such as additional hydroxyapatite (HA) powder, $K_2O$—$Na_2$—$CaO$—$MgO$—$SiO_2$—$P_2O_5$ crystallized glass powder, other bioactive glasses, calcium phosphate, carbon, graphite, aramid, bone particles, bone chips, polyethylene, titanium, other metals, ultra high weight polyethylene, polymethylmethacrylate fibers in a cement matrix, tricalcium phosphate, and hydroxycarbonate apatite, and the like.

A common means of evaluating strength of bone filling cements is to use X-Ray Diffraction Spectroscopy (XRD). Alternatively, FTIR (Fourier Transform Infrared Spectroscopy) can be used. Measuring samples using XRD and FTIR are well known to one of ordinary skill in the art. For an example of XRD and FTIR measurements in bone cement, please see U.S. Pat. No. 5,914,356, which is herein incorporated by reference in its entirety for all purposes. A commonly used method in both XRD and FTIR involves taking spectroscopic samples of explanted bone material for observation.

Typical strengths of the cements of the present invention were found to be between about 0.5 and about 2.5 MPa. The strengths of the cements can be increased by adding the above mentioned re-enforcing materials. The amount that is added is dependent on where the bone cement formulation is to be used and whether or not those bones are load bearing bones. For example, if it is to be used on vertebral bones, one might add sufficient re-enforcing materials to attain a strength of 2-12 MPa.

It is contemplated and therefore within the scope of the invention that the bone cement can be used in conjunction with one or more bone surgical screws, metal rods or plates (such as titanium rods or plates), NITINOL alloy structural devices, and/or other mechanical structural devices that add structural strength to the bone. When these structural devices are used, the cement may be used with or without one or more of the above-identified re-enforcing agents. When the bone cement formulation is used without one or more re-enforcing agents, the bone cement serves, in essence, as a lattice that allows accretion of bone into the macroscopic voids. The accretion of bone into the lattice (in combination with the bone cement formulation) may lead to bone that has greater structural strength.

Mixing antibiotics or other biologically useful compounds into the cement will prevent the development of infections or serve some other useful biological purpose when the bone undergoes accretion into the macroscopic voids.

EXPERIMENTAL

A dry mixture of 60 g tricalcium phosphate (TCP), 20 g strontium hydrophosphate ($SrHPO_4$), 10 g strontium carbonate ($SrCO_3$), 3 g precipitated hydroxyapatite (pHA), and 0.93 to 4.65 g of sodium phosphate dibasic ($Na_2HPO_4$), is combined. 0.5 to 5% w/w (of dry constituents) of a cohesion promoter is optionally added to the dry mixture. The dry mixture is mixed with a 1 to 1 solution of potassium phosphate buffer containing 4M dipotassium phosphate dibasic and 1.5M potassium phosphate monobasic ($K_2HPO_4$ (4M) and $KH_2PO_4$ (1.5M)) pH≈6.8). The liquid to powder ratio is about 0.33 to 0.35 ml. liquid to 1.0 gram powder. The outgassing of $CO_2$ in the slightly acidic mixture from the carbonate generates internal bubbles in the mixture, yielding a foamed structure upon curing of the cement. This foamed structure is then ready for use as bone filler.

In an alternative embodiment, the following components are added in the dry element to generate the bone cement:
30 g TCP
10 g $Sr_3(PO_4)_2$
10 g $SrHPO_4$
5 g $SrCO_3$
10 g $K_2HPO_4$
added to a 1:1 mixture of $K_2HPO_4$ (3M) $KH_2PO_4$ (1M)) pH≈6.7.

In another embodiment, the following components are added in the dry element to generate the bone cement:
30 g TCP
10 g $Sr_3(PO_4)_2$
10 g $SrHPO_4$
5 g $SrCO_3$
10 g $K_2HPO_4$
added to a 1:1 mixture of $K_2HPO_4$ (3M) $KH_2PO_4$ (1M)) pH≈6.7. The L/P (liquid to powder) ratio is 0.22.

In another embodiment, the following components are added in the dry element to generate the bone cement:
60 g TCP
12 g $Sr_3(HPO_4)_2$
6 g $SrHPO_4$
3 g $SrCO_3$
0.5 g $NaHCO_3$
added to a 1:1 mixture of $K_2HPO_4$ (3.5M) $KH_2PO_4$ (1M)) pH≈6.7 at a liquid to powder ratio. The L/P (liquid to powder) ratio is 0.35.

In another embodiment, the following components are added in the dry element to generate the bone cement:
60 g TCP
16 g $Sr_3(HPO_4)_2$
3 g $NaHCO_3$
added to a 1:1 mixture of $K_2HPO_4$ (3.5M) $KH_2PO_4$ (1M)) pH≈6.7 containing monocalcium phosphate monohydrate (MCPM). A 4% solution of $Na_2HPO_4$ and 5% solution of $NaHCO_3$ is used.

Accordingly, in an embodiment, the present invention relates to a bioactive agent or cement composition comprising a dry element and a wet element; wherein said dry element contains tricalcium phosphate, hydroxyapatite and one or more members selected from the group consisting of strontium carbonate and sodium bicarbonate; and said wet element contains a buffer sufficient to keep the bioactive agent or cement composition acidic while curing. The cement in one embodiment is a bone cement.

The composition may contain either of or both of strontium carbonate and sodium bicarbonate. The composition may further strontium hydrophosphate.

In an embodiment, the composition contains 30-70 g tricalcium phosphate (TCP), 10-30 g strontium hydrophosphate ($SrHPO_4$), 3-15 g strontium carbonate ($SrCO_3$), 1-5 g precipitated hydroxyapatite (pHA), 0.5-5 g of sodium phosphate dibasic ($Na_2HPO_4$) 10-30 g $K_2HPO_4$. Further, the composition may further comprise 0.5 to 5% w/w of a cohesion promoter. In an embodiment, the wet element is a buffer that is a phosphate buffer.

The pH of the buffer is between 6.5 and 6.9 or alternatively, the buffer has a pH between 6.6 and 6.9, or alternatively, the buffer has a pH that is between 6.6 and 6.8.

The present invention also relates to methods of making a foamed self-curing cement comprising:
mixing together a dry element and a wet element;
wherein the dry element contains tricalcium phosphate, hydroxyapatite and one or more members selected from the group consisting of strontium carbonate and sodium bicarbonate;
and wherein said wet element contains a buffer sufficient to keep the cement composition acidic while curing to generate the foamed self-curing cement.

The dry element contains either or both of strontium carbonate and sodium bicarbonate, and optionally further comprises strontium hydrophosphate.

In an embodiment, the method of present invention has a dry element that contains 30-70 g tricalcium phosphate (TCP), 10-30 g strontium hydrophosphate ($SrHPO_4$), 3-15 g strontium carbonate ($SrCO_3$), 1-5 g precipitated hydroxyapatite (pHA), 0.5-5 g of sodium phosphate dibasic ($Na_2HPO_4$) 10-30 g $K_2HPO_4$. The method optionally employs 0.5 to 5% w/w of a cohesion promoter.

In an embodiment, the method employs a buffer that is a phosphate buffer wherein the pH of the buffer is between 5.0 and 6.9 or alternatively, between 6.0 and 6.9 or alternatively, between 6.5 and 6.9 or alternatively, the buffer has a pH between 6.6 and 6.9, or alternatively, the buffer has a pH that is between 6.6 and 6.8.

In an embodiment, the present invention is also directed to kits containing the above mentioned compositions/bone cements.

An alternative embodiment is directed to a bone piece containing voids wherein the voids contain the above mentioned compositions/bone cements.

The present invention has been described above with regards to a plurality of different embodiments. It is contemplated and therefore within the scope of the present invention that any one or more of the elements discussed above can be combined with any other one or more elements discussed above. It should also be understood that minor modifications can be made to the invention without departing from the scope and spirit of the invention. In addition, where methods and steps described above indicate certain events occurring in certain order, those of ordinary skill in the art will recognize that the ordering of certain steps may be modified and that such modification are in accordance with the variations of the invention. Furthermore, certain steps may be performed concurrently in a parallel process when possible, as well as performed sequentially as describe above. Moreover, when a range is disclosed, it is contemplated and therefore within the scope of the present invention that any real number that falls within the scope of this range is a contemplated endpoint. For example, if a range of 6.5 to 6.9 is given, it is contemplated that an endpoint for the range can be 6.726 even though this real number is not explicitly mentioned. In any event, the present invention is not to be limited by the foregoing written description but is rather to be defined by the following claims.

We claim:

1. A composition comprising a dry element and a wet element;
    wherein said dry element includes tricalcium phosphate, hydroxyapatite, strontium hydrophosphate and one or more members selected from the group consisting of strontium carbonate and sodium bicarbonate; and
    wherein said wet element includes a phosphate buffer sufficient to keep the composition acidic when the dry element and the wet element are initially mixed together.

2. The composition of claim 1, wherein the composition comprises 30-70 g tricalcium phosphate (TCP), 10-30 g strontium hydrophosphate ($SrHPO_4$), 3-15 g strontium carbonate ($SrCO_3$), 1-5 g precipitated hydroxyapatite (pHA), 0.5-5 g of sodium phosphate dibasic ($Na_2HPO_4$), and 10-30 g $K_2HPO_4$.

3. The composition of claim 2, further comprising 0.5 to 5% w/w of a cohesion promoter.

4. The composition of claim 1, wherein the pH of the buffer is between 6.5 and 6.9.

5. A bone cement comprising:
    a dry element comprising tricalcium phosphate, hydroxyapatite, strontium hydrophosphate and one or more members selected from the group consisting of strontium carbonate and sodium bicarbonate; and
    a wet element comprising a phosphate buffer sufficient to keep the composition acidic when the dry element and the wet element are initially mixed together, wherein the calcium phosphate cement is configured for placement in a void inside a bone in a patient's body, and wherein the calcium phosphate cement, when cured, forms macroscopic pores of varying sizes and densities with sufficient surface area to provide regions for bone remodeling.

6. The bone cement of claim 5, wherein the macroscopic pores are between about 4 and 200 microns in diameter.

7. The bone cement of claim 5, wherein the calcium phosphate bone cement is made from a composition that comprises a wet element and a dry element and the dry element includes 30-70 g tricalcium phosphate (TCP), 10-30 g strontium hydrophosphate ($SrHPO_4$), 3-15 g strontium carbonate ($SrCO_3$), 1-5 g precipitated hydroxyapatite (pHA), 0.5-5 g of sodium phosphate dibasic ($Na_2HPO_4$), and 10-30 g 10-30 g $K_2HPO_4$.

8. The bone cement of claim 5, wherein the phosphate buffer is buffered to a pH of between about 6.5 and 6.9.

9. The bone cement of claim 5, further comprising 0.5 to 5% w/w of a cohesion promoter.

10. The bone cement of claim 5, further comprising an antibiotic.

11. The bone cement of claim 10, wherein the antibiotic is one or more members selected from the group consisting of gentamicin, gentamicin sulfate, erythromycin, tobramycin, vancomycin, cefazolin, oxacillin, cefotaxime, colistin, clindamycin, and fusidic acid.

12. A method of making a bone cement comprising:
mixing together a dry element and a wet element;
wherein said dry element includes tricalcium phosphate, hydroxyapatite, strontium hydrophosphate and one or more members selected from the group consisting of strontium carbonate and sodium bicarbonate; and
wherein said wet element includes a phosphate buffer sufficient to keep the cement composition acidic during the initial curing to generate a foamed cement.

13. The method of claim 12, wherein the dry element contains both strontium carbonate and sodium bicarbonate.

14. The method of claim 12, wherein the dry element contains 30-70 g tricalcium phosphate (TCP), 10-30 g strontium hydrophosphate ($SrHPO_4$), 3-15 g strontium carbonate ($SrCO_3$), 1-5 g precipitated hydroxyapatite (pHA), 0.5-5 g of sodium phosphate dibasic ($Na_2HPO_4$, and 10-30 g $K_2HPO_4$.

15. The method of claim 12, further comprising 0.5 to 5% w/w of a cohesion promoter.

16. The method of claim 12, wherein the pH of the buffer is between 6.5 and 6.9.

17. The method of claim 12, wherein the bone cement is self curing.

18. A kit comprising a dry element and a wet element, wherein when the dry element comprises tricalcium phosphate, hydroxyapatite, strontium hydrophosphate and one or more members selected from the group consisting of strontium carbonate and sodium bicarbonate and the wet element comprises a phosphate buffer sufficient to keep the composition acidic when the dry element and the wet element are initially mixed together resulting in a foamed cement that is suitable for bone remodeling.

19. The kit of claim 18 further comprising an antibiotic.

20. The kit of claim 19, wherein the antibiotic is one or more members selected from the group consisting of gentamicin, gentamicin sulfate, erythromycin, tobramycin, vancomycin, cefazolin, oxacillin, cefotaxime, colistin, clindamycin, and fusidic acid.

* * * * *